Figure 1:
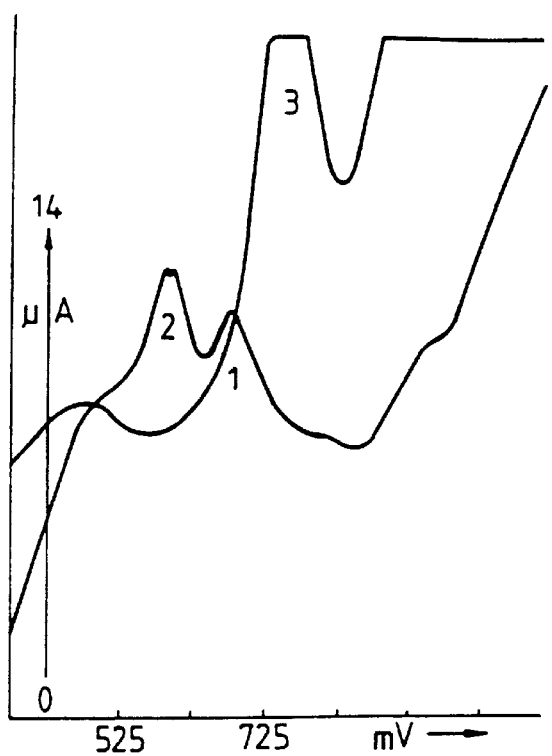

United States Patent [19]

Jackman et al.

[11] Patent Number: 5,807,687
[45] Date of Patent: Sep. 15, 1998

[54] DETECTION OF CNS DISEASE

[75] Inventors: Roy Jackman; Sally J. Everest, both of Addleston, United Kingdom

[73] Assignee: Minister of Agriculture, Fisheries and Food in Her Britannic Majesty's Government of the United Kingdom of Great Britain and Northern Ireland, London, England

[21] Appl. No.: 532,635
[22] PCT Filed: Apr. 12, 1994
[86] PCT No.: PCT/GB94/00766
§ 371 Date: Dec. 1, 1995
§ 102(e) Date: Dec. 1, 1995
[87] PCT Pub. No.: WO92/24554
PCT Pub. Date: Oct. 27, 1994

[30] Foreign Application Priority Data

Apr. 13, 1993 [GB] United Kingdom ................... 9307523

[51] Int. Cl.$^6$ .................... G01N 33/53; G01N 33/00; A61K 49/00
[52] U.S. Cl. ................. 435/7.1; 424/9.1; 424/9.2; 436/91; 436/99
[58] Field of Search .................. 424/9.1, 9.2; 436/99; 435/7.1

*Primary Examiner*—James C. Housel
*Assistant Examiner*—Rodney P. Swartz
*Attorney, Agent, or Firm*—Nixon & Vanderhye P.C.

[57] ABSTRACT

Techniques for the detection of disease of the central nervous system, particularly of bovine spongiform encephalopathy or "mad cow disease", scrapie and related states, are provided based upon the detection of a factor present in the urine of affected animals or humans. That factor is defined in terms of elution data from an ion exchange column and by electrochemical characteristics.

11 Claims, 1 Drawing Sheet

DETECTION OF CNS DISEASE

The present invention relates to techniques for the detection of disease of the central nervous system, particularly bovine spongiform encephalopathy, scrapie, Jacob-Creuzfeld syndrome and related states.

It has been noted that serotonin levels are reduced in the blood of scrapie infected sheep (Chatelain et al (1984) CR Soc. Biol. 178, 664–670, and that some electrochemical changes occur in the urine of such sheep (Combrisson et al (1991) Bull. Acad. Vet. de France 64, 257–266; Banissi-Sabourdy et al (1992) Bioelectrochem & Bioenergetics 28, 127–147, but no reliable test has resulted from these findings.

At present there is no diagnostic test available for the screening of animals, including humans, for spongiform encephalopathy type disease and the confirmation of its presence is usually by direct observation of tissues in autopsy. There remains a particular need for a method of screening live animals, particularly prior to slaughter for consumption purposes, and preferably before their milk is consumed, and most preferably for a non-invasive test. The present inventor has now identified a factor present in the biological fluids of affected animals, particularly their urine, the amount of which correlates well with the occurence of these diseases.

The present invention provides a method for determining the presence of central nervous system disease in a human or animal body by analysis of one or more of its biological fluids characterised in that the fluid is analysed for the presence of a factor associated with a fraction obtainable from an ethanol extract of urine from animals having the disease, that fraction being elutable from a 0.2M Tris buffer pH 7.0 equilibrated DEAE-Sepharose Cl ion exchange column (particularly a CL6B) increasing gradient elution using from 0 to 0.2M sodium chloride in 0.02M Tris buffer pH 7.0; the fraction being elutable with between 0.08M and 0.015M sodium chloride, particularly between 0.08M and 0.09M sodium chloride in Tris buffer pH 7.0; wherein the amount of this factor is related to presence of the disease state.

The most convenient method for detecting this 'disease' factor may of course vary depending upon the fluid to be tested, eg. whether CSF fluid, whole blood or a fraction thereof, or urine. The sampling of urine renders the test suitable for routine screening by electro-chemical detection means and can avoid the need for invasive methods. Other tests, eg. colorimetric and immunological, will also be applicable.

A preferred aspect of the present invention relates the amount of the 'disease factor' with the amount of one or more reference factors present in the fluid, particularly in urine, and uses the ratio of these to indicate disease presence. These reference factors are a reference factor (2) that is associated with a fraction elutable with between 0.09 and 0.13M sodium chloride, and a reference factor (3) associated with a fraction elutable with between 0.13 and 0.2M sodium chloride; both using the ion-exchange column technique described above and the same ethanol extract of disease animal's urine.

The second reference factor (3) has been found to be uric acid, the first reference factor (2) has been found to have properties associated with tyrosine or a precursor or derivative thereof having at least one, and possibly two or three, phenolic groups including one phenol group para to a substitute side chain. It should be realised that the amount of material isolatable from urine is very small and has so far proven difficult to identify.

The disease factor (1) has been found to have properties consistent with having a substituted phenyl or histidine nucleus, also with a para-hydroxy substituent and at least one methyl substituent.

Both disease factor (1) and reference factor (2) have similar physical properties. Both are water soluble and soluble in methanol and ethanol, both are bound to aminopropyl solid phase extraction columns but only reference factor (2) can be desorbed using 0.5M HCl in 50:50 methanol/water; thus in this way reference factor can be separated from disease factor. The disease factor does not come off this column in either 100% methanol or 1:1 methanol:5M HCl in water. Both reference factor (2) and disease factor (1) are bound to anion exchange material such as DEAE-Sepharose, being eluted with between 0.08 to 0.15M sodium chloride, the reference factor being desorbed slightly after the disease factor, ie. above 0.09M as described above. The reference factor (2) may be further identified by its Rf factor on TLC RP18 plates using an 80:20 water-:methanol solvent.

It has been found that measurement of the difference in height of an electrochemically measured peak obtained relating to the amount of reference factor (2) and one obtained relating to the disease factor, divided by the difference in height of peaks relating to the reference factors (2) and (3), provides a value indicative of disease state. Initial investigation shows that values of 1.0 or more correlate with absence of disease while less than 1.0 correlates with disease status. It will be appreciated that any method that measures the relative concentrations of disease factor and one or both of these reference factors may be used to indicate presence of the aforesaid diseases. Furthermore, it will be realised that in some disease formats, the disease factor may occur in an altered form while still retaining its basic chemical characteristics; eg. as a conjugate or metabolite. Such variations of the factor will also be targetable for the purposes of detection and thus the present invention relates to their targeting in so far as they are so related and correlate to the diseases of interest.

In a further aspect of the present invention there is provided a test kit for determining the presence of central nervous system disease comprising one or more reagents capable of specifically detecting the disease factor described above.

Most conveniently these agents will be specific binding assay agents capable of specific detection of the approximate amount of the disease agent in a biological fluid. Typically such agents will be antibodies raised to immunogens formed from the purified fraction obtained by its elution from a column, eg using 0.08 to 0.09M NaOH in 0.02M Tris buffer from a DEAE column as described above. Such antibodies may be monoclonal antibodies or polyclonal antibodies raised in the known manner using suitably selectable immunogen design, eg ovalbumen conjugate, and adjuvant if necessary as will be determined by simple bench experimentation; the antibodies being conventionally labelled for detection of disease agent in the known manner. Alternatively the test reagents may include specific chemical test agents for the agent.

Isolation of the fraction containing the disease factor and the application of electrochemical techniques to the method of the invention will be illustrated by way of the non-limiting examples and related Figures provided below.

FIGURES

FIG. 1: shows a voltammogram of a sample derived from BSE positive urine as obtained using the method of Example 1.

Figure 2:
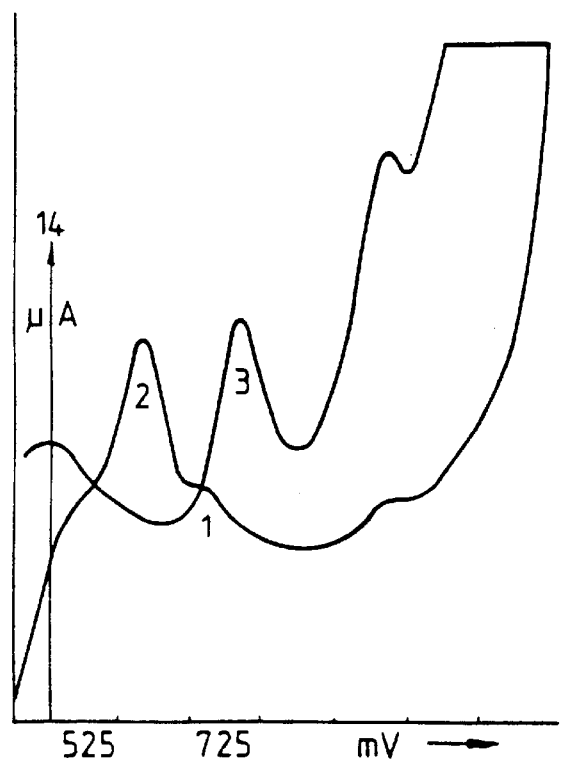

FIG. 2: shows a voltammogram of a sample derived from BSE negative urine as obtained using the method of Example 1.

EXAMPLE 1

Urine samples were taken from animals (cattle) under investigation and screened using a commercial electrode cell (ESA Analytical: Coulochem II, 5010 electrode assembly) containing three porous carbon electrodes, these being a reference electrode, a working electrode and a secondary electrode. The sample was prepared by mixing 200 µl of urine with 768 µl deionised water and 32 µl hydrochloric acid (10.8N) (or concentrated sulphuric acid) in order to acidify it prior to introduction into the electrode cell. The cell was operated using the following electrical parameters:

Applied potential cycles:
  (i) 175 mV to 1325 mV
  (ii) 1325 mV to 175 mV

These cycles were repeated one or more times and the voltage change rate used was usually 10 mV/second, although any rate in the range eg. 1–100 mV/second was found to be usable. The induced current was measured at 20 µamps full scale deflection but 2–200 µamps f.s.d. may be conveniently used. The output of the cell electrodes was transcribed to a X-Y linear plotter.

Results

Three peaks were produced on the plotter output;

(a) Primary Peak 1: occurs only on the second and subsequent cyclic sweeps during increasing applied voltage between 650 and 850 mV (mean at 750 mV); this being referred to also as disease correlating peak.

(b) Reference Peak 2: occurs only on the second and subsequent cyclic sweep during increasing applied voltage at approximately 100 mV lower than the Primary Peak 1.

(c) Reference Peak 3: occurs only on the first cyclic sweep during increasing applied voltage at approximately 25 to 100 mV higher than the Primary Peak 1, this being resultant from irreversible oxidation and being found to correspond to uric acid.

Quantitation

The Primary Peak 1 is found to be increased in the diseased state but because urine from different animals, whether captured mid-flow, by cannula or from post-mortem bladders, varies considerably in concentration/dilution. Reference peaks 2 and 3 were used to normalise readings by serving as internal standards relating to urine dilution within the sample.

Thus the difference in height of the Primary Peak 1 and Reference Peak 2 divided by the difference in height of the Reference Peaks 2 and 3, provides a determining numerical value indicative of disease state:

Peak 2–Peak 1/Peak 3–Peak 2 greater than or equal to 1.0—Sample Negative

Peak 2–Peak 1/Peak 3–Peak 2 less than 1.0—Sample Positive

Assessment of Test

A trial was run using blind samples analysed by the test as described above and the results compared to histopathological diagnosis results, the results of which are provided in Table 1 wherein positive identifications of disease state are indicated by + and negative identifications by –.

TABLE 1

| Sample | Urine | Histol | Sample | Urine | Histol |
|---|---|---|---|---|---|
| 1 | + | + | 10 | – | – |
| 2 | – | – | 11 | + | + |
| 3 | + | + | 12 | + | + |
| 4 | +/– | + | 13 | + | + |
| 5 | + | + | 14 | + | + |
| 6 | – | – | 15 | + | + |
| 7 | + | + | 16 | + | + |
| 8 | + | + | 17 | + | + |
| 9 | + | + | 18 | + | + |

EXAMPLE 2

Urine from diseased cattle was subjected to a number of isolation procedures to provide purified fractions containing the identified disease correlating factor. One preferred procedure is as follows:

(a) Ethanol extraction: Inorganic salts and ethanol insoluble compounds were precipitated from urine by addition of 4×volume of absolute ethanol and filtering off the precipitate. The filtrate was evaporated to dryness and the compounds of interest redissolved in ethanol, evaporated to dryness again and taken up in 0.02M Tris buffer at pH 7.0 for a separation stage (b).

(b) The sample from step (a), obtained from 50 ml of urine, was absorbed onto a DEAE-Sepharose CL6B (Pharmacia) ion exchange column previously equilibrated with 0.2M Tris buffer pH 7.0. The column was washed clear of non-adsorbing material and subjected to an increasing gradient elution from 0 to 0.2M sodium chloride in 0.02M Tris buffer pH 7.0.

4 ml fractions were collected and assessed for activity on the electrochemical detector. Peak 1 was eluted between 0.08 and 0.09M sodium chloride and found to be essentially electrochemically pure. Peak 2 was eluted at between 0.09 and 0.13M sodium chloride and was also found to be electrochemically pure. Peak 3 was eluted at between 0.13 and 0.2M sodium chloride. The exact elution salt concentration required appears to depend on the amount of original urine and its original concentration.

We claim:

1. A method for determining the presence of a transmissible spongiform encephalopathy in a nonhuman animal wherein its urine is analyzed for the presence of a disease factor (1) an increase in the amount of which is related to presence of the disease state, wherein said disease factor (1);

(a) has properties consistent with its having a substituted phenyl or histidine nucleus, (b) is associated with a fraction obtainable from an ethanol extract of urine obtained from animals having Bovine spongiform encephalopathy, that fraction being elutable from a 0.2M Tris buffer pH 7.0-equilibrated DEAE-Sepharose Cl ion exchange column by increasing gradient elution from 0.08 and 0.09M sodium chloride in 0.02M Tris buffer pH 7.0, (c) is detectable in that fraction by means of its electrochemical properties, and has mid-point potential of between 650 and 850 mV, (d) is soluble in water, methanol and ethanol, and (e) can be bound to aminopropyl solid phase extraction columns, but is not recoverable from said column using 100% methanol or 5M aqueous HCl/methanol 1:1 mixture as eluant.

2. A method as claimed in claim 1 wherein the disease factor (1) has a para-hydroxy substituent and at least one methyl substituent.

3. A method as claimed in claim 1 wherein the amount of the disease factor (1) is compared with the amount of a reference factor (2) that:
  (a) is associated with an ethanol extractable urine fraction, that fraction being elutable from a 0.2M Tris buffer pH 7.0-equilibrated DEAE-Sepharose Cl ion exchange column by increasing gradient elution using from 0.09 and 0.13M sodium chloride in 0.02M Tris buffer pH 7.0,
  (b) is detectable in that fraction by means of its electrochemical properties, and has mid-point potential approximately 100 mV lower than that of the disease factor (1), and
  (c) is soluble in water, methanol and ethanol, and can be bound to an aminopropyl solid phase extraction column, but is recoverable from said column using 0.5M HCl in 50:50 methanol/water.

4. A method as claimed in claim 3 wherein reference factor (2) has properties associated with tyrosine or a precursor or derivative thereof having at least one phenolic group.

5. A method as claimed in claim 3 wherein reference factor (2) includes one phenol group para to a substitute side chain.

6. A method as claimed in claim 3 wherein the disease factor (1) is electrochemically measured.

7. A method as claimed in claim 3 wherein the amount of the disease factor is compared with the amount of a reference factor (3) that is uric acid.

8. A method as claimed in claim 7, wherein the disease factor (1), reference factor (2) and reference factor (3) are electrochemically measured and the difference in height of peak obtained relating to the amount of reference factor (2) and that obtained relating to the disease factor (1), is divided by the difference in height of peaks relating to the reference factors (3) and (2), and the value obtained is used to determine disease state.

9. A method as claimed in claim 8 wherein the disease factor (1), reference factor (2) and reference factor (3) are eluted from an ion exchange column prior to electrochemical measurement.

10. A method as claimed in claim 9 wherein the ion exchange column contains DEAE-Sepharose CL6B.

11. A method of generating antibodies for use in a method of diagnosis of a transmissible spongiform encephalopathy in a nonhuman animal, comprising:
  (a) purifying the disease factor (1) of claim 1 from the fraction obtainable from an ethanol extract of urine obtained form animals having Bovine spongiform encephalopathy, that fraction being elutable from a 0.2M Tris buffer pH 7.0 equilibrated DEAE-Sepharose Cl ion exchange column by increase gradient elution from 0.08 and 0.09 sodium chloride in 0.02M Tris buffer pH,
  (b) administering the disease factor (1) to an animal in the form of an immunogen conjugate, and
  (c) recovering antibodies from that animal.

* * * * *